United States Patent [19]
Koehler et al.

[11] Patent Number: 5,568,910
[45] Date of Patent: Oct. 29, 1996

[54] ANESTHESIA MACHINE

[75] Inventors: Raymond Koehler, Whitehouse Station; James E. Donaldson, Neptune, both of N.J.

[73] Assignee: Delmarva Laboratories, Inc., Midlothian, Va.

[21] Appl. No.: 397,671

[22] Filed: Mar. 2, 1995

[51] Int. Cl.$^6$ .................................................. F16K 15/18
[52] U.S. Cl. ...................... 251/83; 128/205.24; 128/910; 137/522; 137/523
[58] Field of Search .................................. 137/522, 523, 137/524, 543.17, 469, 535, 540, 543.13; 128/205.24, 910; 251/82, 83; 604/247

[56] References Cited

U.S. PATENT DOCUMENTS

| | | | |
|---|---|---|---|
| 526,176 | 9/1894 | Blair | 251/83 |
| 954,180 | 4/1910 | Giffen | 137/522 |
| 1,044,106 | 11/1912 | Vidar | 137/524 |
| 1,656,670 | 1/1928 | Greenhouse | 137/524 |
| 2,292,294 | 8/1942 | Rotter et al. | 137/469 |
| 2,674,260 | 4/1954 | Thrush | 137/469 |
| 2,861,569 | 11/1958 | Emerson | 251/83 |
| 2,968,295 | 1/1961 | Haller | 137/469 |
| 3,212,523 | 10/1965 | Martin | 137/596.13 |
| 3,292,895 | 12/1966 | Leger et al. | 251/83 |
| 3,426,794 | 2/1969 | Freytag | 128/205.24 |
| 3,568,695 | 3/1971 | DeFrees | 137/493.6 |
| 3,604,448 | 9/1971 | Marrese | 128/205.24 |
| 3,636,966 | 1/1972 | Aldrich et al. | 137/469 |
| 3,719,401 | 3/1973 | Peruglia | 137/517 |
| 3,800,793 | 4/1974 | Marrese et al. | 137/526 |
| 3,981,328 | 9/1976 | Yonezawa | 251/83 |
| 4,039,139 | 8/1977 | Bird | 251/82 |
| 4,044,793 | 8/1977 | Krueger et al. | 137/508 |
| 4,406,302 | 9/1983 | Olesen | 137/514.5 |
| 4,941,504 | 7/1990 | Beauvir | 251/83 |
| 4,967,791 | 11/1990 | Sternberger | 137/522 |
| 5,016,627 | 5/1991 | Dahrendorf et al. | 128/205.24 |
| 5,165,445 | 11/1992 | Vertanen | 137/493.6 |

FOREIGN PATENT DOCUMENTS

| | | | |
|---|---|---|---|
| 403255 | 9/1909 | France | 251/82 |
| 1010835 | 6/1957 | Germany | 128/205.24 |

*Primary Examiner*—George L. Walton
*Attorney, Agent, or Firm*—Finnegan, Henderson, Farabow, Garrett & Dunner

[57] ABSTRACT

An anesthesia machine includes a breathing system for delivering a gas mixture, including an anesthetic gas, to a patient for inhalation and for collecting exhaled gas from the patient. A cannister flow communicates with the breathing system and removes carbon dioxide from the exhaled gas. A pressure relief valve includes a housing that defines a chamber in flow communication with the breathing system, a valve member for regulating a flow of gas from the breathing system into the chamber and venting gas into the chamber when pressure in the breathing system exceeds a pressure threshold setting, and a plunger for preventing the flow of gas into the chamber independent of the pressure in the breathing system without changing the pressure threshold setting. The cannister, pressure relief valve, and other components are secured to a manifold having internal flow channels.

28 Claims, 6 Drawing Sheets

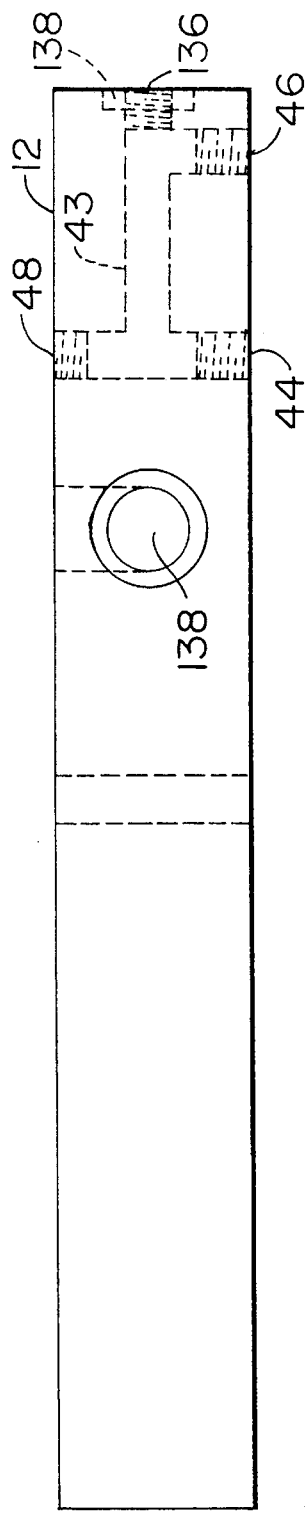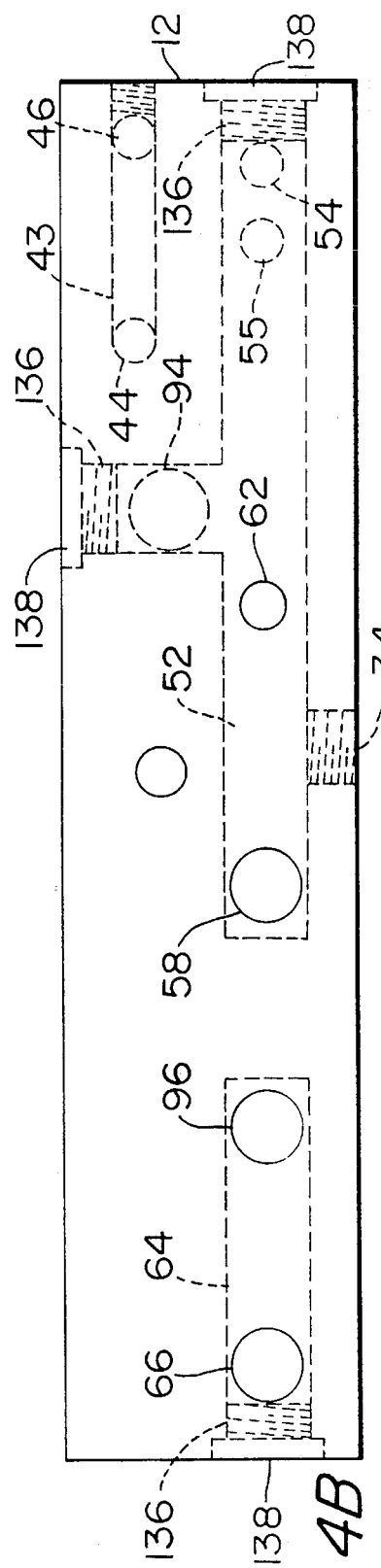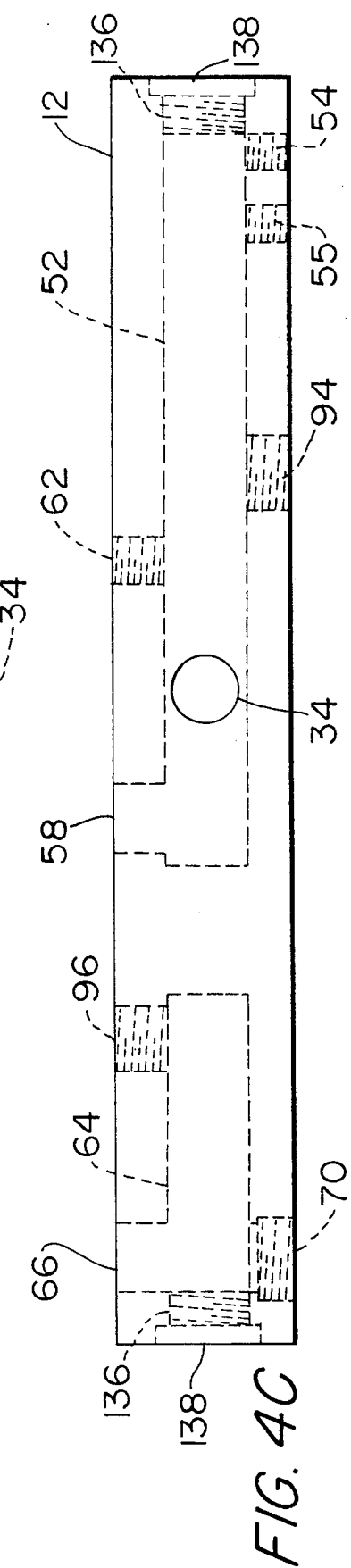

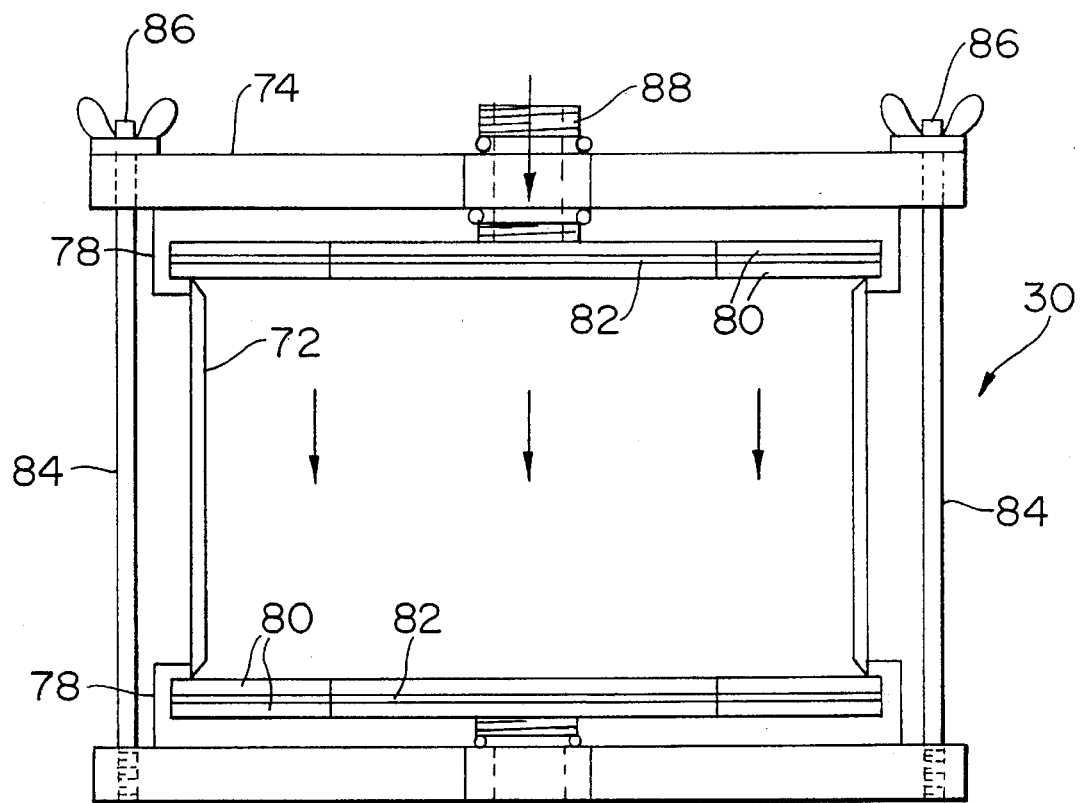
FIG. 5
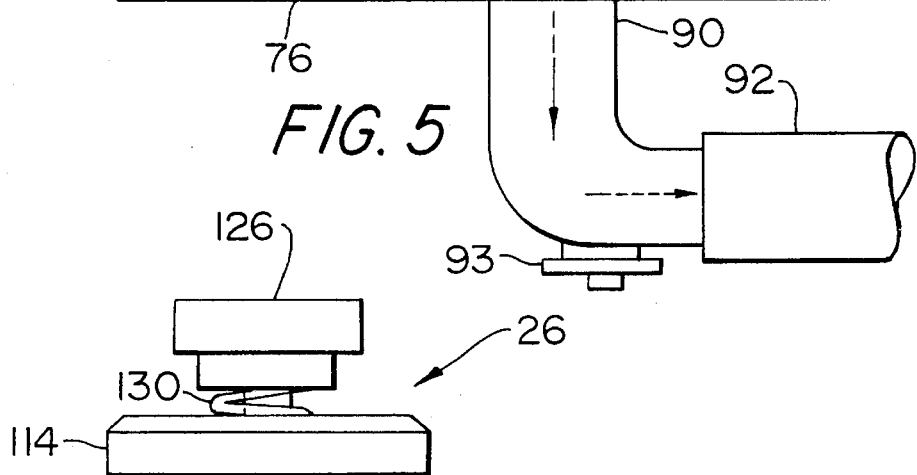
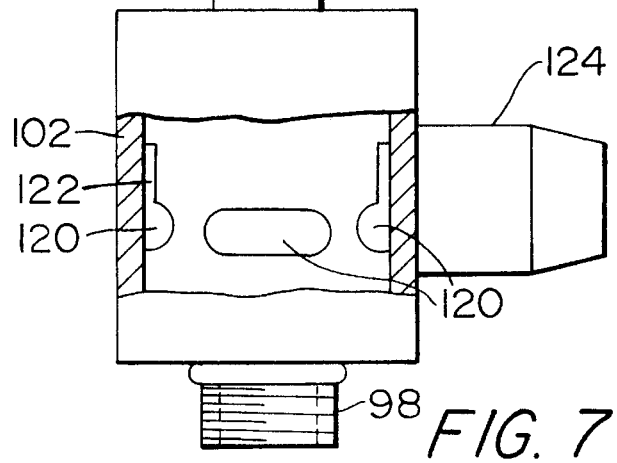
FIG. 7

ANESTHESIA MACHINE

BACKGROUND OF THE INVENTION

1. Field of the Invention

The present invention relates generally to anesthesia machines and, more particularly, to an anesthesia machine having a pressure relief valve with vent override capabilities. The present invention also relates to an anesthesia machine having a manifold with modular components, including a carbon dioxide absorber that is easy to clean and reseal.

2. Discussion of the Related Art

Anesthesia machines typically include a substantially closed breathing system that provides an oxygen/anesthesia gas mixture to the patient for inhalation and receives and processes exhaled gas from the patient for recirculation. The breathing system processes the exhaled gas by removing carbon dioxide from the gas and merges this processed exhaled gas with the flow of the oxygen/anesthesia gas mixture. The breathing system interfaces with the patient via inhalation and exhalation tubes connected to a breathing mask or other patient interface.

The breathing system is not completely closed since fresh anesthesia gas and oxygen are continually supplied to the breathing system from an external source. Therefore, a pressure relief or pop-off valve communicates with the breathing system and evacuates excess gas from the breathing system to compensate for the fresh gas entering the system when pressure in the system exceeds a predetermined level. The vented gas is preferably collected by a closed vacuum system rather than released to the atmosphere to avoid exposure of the gas to operating room personnel.

Conventional pressure relief valves typically include a valve closure element that is spring biased against a valve seat. When a predetermined pressure is applied beneath the valve closure, it is lifted from the seat and gas is vented from the breathing system through an outlet port. The pressure threshold at which the valve opens is adjustable by varying the biasing force on the valve, which is usually accomplished by rotating an adjustment knob threadably secured to a valve housing to selectively compress the bias spring against the valve closure element.

The breathing system also typically includes an expandable member, such as a breathing bag, for receiving gas exhaled by the patient. The bag inflates during exhalation and deflates during inhalation. If the patient stops breathing, the bag may be squeezed to force gas into the patient's lungs in order to stimulate breathing. The pressure relief valve must be fully closed during this procedure, referred to as "bagging," so that gas flows into the patient's lungs rather than escaping through the pressure relief valve.

Since "bagging" is usually performed in emergency situations, reaction time is critical; therefore the pressure relief valve must be quickly closed. As a result, the adjustment knob is coarsely threaded and usually requires only three rotations to move between maximum and minimum bias positions.

The pressure relief valve must also be able to precisely set the pressure threshold for the breathing system. Coarsely threaded adjustment knobs, however, sacrifice precision and it can be quite troublesome to precisely achieve the desired pressure threshold. In fact, users commonly forego setting the pressure threshold with the adjustment knob, and instead set the valve to the minimum bias position (i.e., minimal pressure required to unseat the valve member) and increase the oxygen flow as much as three times the normal requirement. While this practice may be sufficient, it greatly increases consumption costs since tripling the oxygen flow rate also triples the anesthesia consumption rate. Considering that an anesthetic such as isofluorine costs about $65 per 3 oz., such a practice is quite costly.

Finely threaded adjustment knobs provide more precision since a slight turn of the adjustment knob will only vary the pressure setting by a small increment. However, they require five or six turns to adjust the spring to maximum bias, thus wasting valuable time when "bagging" is necessary.

In addition to the above drawbacks, the knob, regardless of whether it is finely-threaded or coarsely-threaded, must be rotated from the maximum bias position back to the previous bias setting after "bagging" to reset the pressure threshold for the system. As a result, additional time and effort is required.

In light of the above drawbacks, there is a significant need for a pressure relief valve that can be precisely adjusted to a desired pressure threshold setting and can be quickly positioned to prevent venting and then quickly returned to the desired pressure threshold setting.

Conventional anesthesia machines also suffer from disadvantages in that the components of the breathing system, e.g., check valves, a manometer, flowmeters, a carbon dioxide absorber, and a pressure relief valve, are typically interconnected with several segments of flexible tubing or rigid conduits having bends or other configurations that are difficult to clean. As a result, substantial time and effort is required to thoroughly clean the breathing system. Otherwise, contaminants may remain in the system, thus posing risk to the patient.

In addition to cleaning the flow paths of the breathing system, individual components may require disassembly for cleaning. For example, the carbon dioxide absorber, which generally includes a cannister and lid, must be cleaned by removing the carbon dioxide absorbing material (e.g., calcium hydroxide) from the cannister and replacing it with a fresh supply. Since a tight seal between the lid and cannister must be maintained during use, it is imperative that the seal between the lid and cannister be effectively reestablished. Since conventional designs render it difficult to correctly and easily align the lid with the cannister, the integrity of the seal and the breathing system is jeopardized.

SUMMARY OF THE INVENTION

The present invention is directed to an anesthesia machine that substantially obviates one or more of the problems due to limitations and disadvantages of the related art.

Additional features and advantages of the invention will be set forth in the description which follows, and in part will be apparent from the description, or may be learned by practice of the invention. The objectives and other advantages of the invention will be realized and attained by the system particularly pointed out in the written description and claims, as well as the appended drawings.

To achieve these and other advantages and in accordance with the purpose of the invention, as embodied and broadly described herein, the anesthesia machine includes a breathing system for delivering a gas mixture, including an anesthetic gas, to a patient for inhalation and for collecting exhaled gas from the patient; means, in flow communication with the breathing system, for removing carbon dioxide from the exhaled gas; and a pressure relief valve having a housing that defines a chamber in flow communication with the breathing system, a valve member for regulating a flow of gas from the breathing system into the chamber and venting gas into the chamber when pressure in the breathing system exceeds a threshold setting, and vent override means for preventing the flow of gas into the chamber independent of the pressure in the breathing system without changing the pressure threshold setting.

In another aspect, the breathing system of the anesthesia machine includes a manifold having a first internal channel formed therein for receiving the gas mixture for inhalation by the patient and a second internal channel formed therein for receiving the exhaled gas from the patient.

In yet another aspect, the carbon dioxide removing means of the anesthesia machine includes a cannister comprising a casing open at its top and bottom ends, first and second mounting plates for covering the top and bottom ends of the casing, a first seal supported by the first mounting plate and a second seal supported by the second mounting plate, and a plurality of rods secured to and extending from one of the first and second mounting plates and receivable in openings in the other of the first and second mounting plates for joining the mounting plates with the casing therebetween, the first and second seals engaging top and bottom edges of the casing to effectively seal the cannister.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

BRIEF DESCRIPTION OF THE DRAWINGS

FIGS. 4A–4C are rear, plan, and front views of the manifold shown in FIG. 3.

FIG. 5 is a front view of a carbon dioxide absorber for the anesthesia machine of FIG. 1.

FIG. 7 is a front view of the pressure relief valve of FIG. 6, partially cut-away to show an inner wall of the valve.

DESCRIPTION OF THE PREFERRED EMBODIMENT

Figure 1:
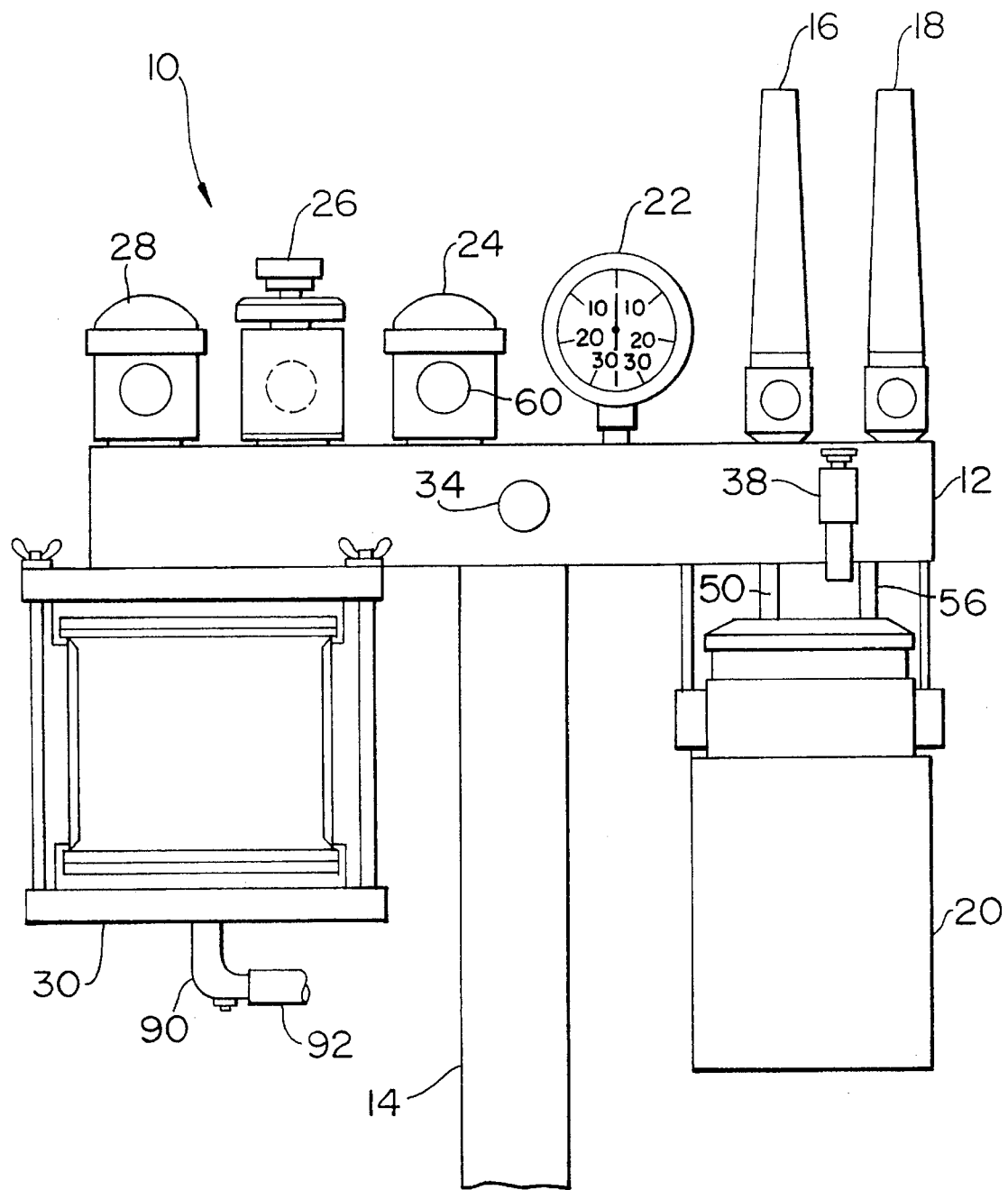
FIG. 1 is a front view of an anesthesia machine of the present invention.

Reference will now be made in detail to the present preferred embodiment of the invention, an example of which is illustrated in the accompanying drawings. Wherever possible, the same reference characters will be used throughout the drawings to refer to the same or like parts.

An exemplary embodiment of the anesthesia machine of the present invention is shown in FIG. 1 and is designated generally by reference numeral 10. The anesthesia machine 10 includes a manifold 12 attached to a stand 14, which allows for height adjustment of the manifold 12.

Figure 2:
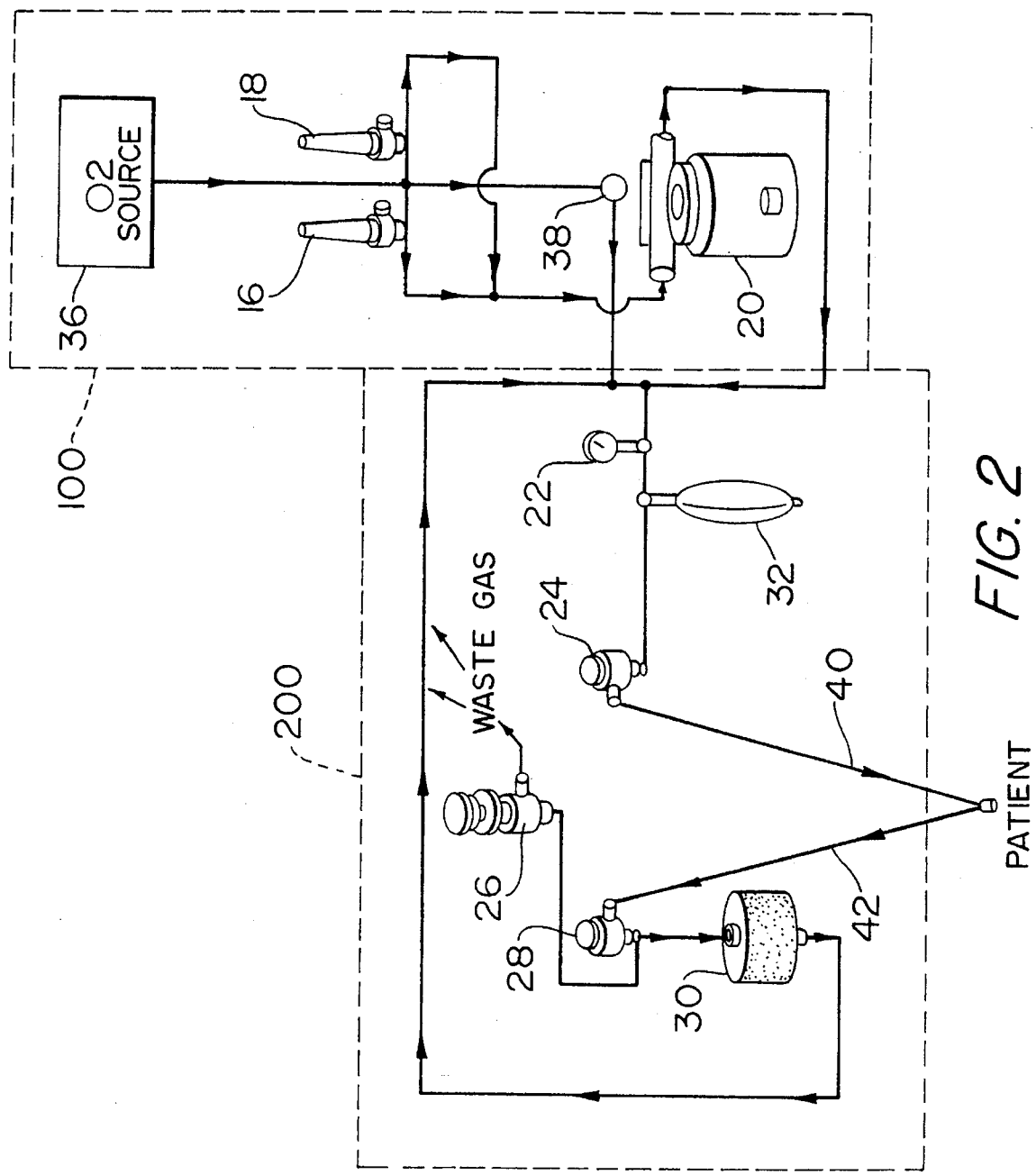
FIG. 2 is a flow diagram of a patient breathing system for the anesthesia machine of FIG. 1.

Removably secured to the manifold are flowmeters 16 and 18, a vaporizer 20, a manometer 22, an inhalation valve 24, a pressure relief valve 26, an exhalation valve 28, and a carbon dioxide absorber 30. A breathing bag 32, which is shown schematically in FIG. 2, is also connected to the manifold 12 via a port 34. These components, which are in fluid flow communication with each other as shown in FIG. 2, comprise a patient breathing system for the anesthesia machine 10.

FIG. 2 is a flow diagram of the patient breathing system that essentially includes two subsystems: (1) an oxygen/ anesthesia gas delivery system 100 for mixing oxygen and anesthesia at a preset ratio; and (2) a closed loop recirculation system 200 for providing the patient with the oxygen/ anesthesia gas mixture and collecting and recirculating gases exhaled by the patient. The breathing system is particularly suited for veterinary use, but may be adapted for human use as well.

In the oxygen/anesthesia gas delivery system 100 shown in FIG. 2, oxygen, the rate of which is controlled by flowmeters 16 and 18, flows from an oxygen source 36 into the vaporizer 20, which mixes the oxygen with a predetermined ratio of anesthesia, such as isofluorine. The anesthesia is provided to the vaporizer in liquid form, evaporated by the vaporizer, and mixed with oxygen. The oxygen/anesthesia mixture is then introduced to the recirculation system 200. Alternatively, oxygen can be directly supplied to the recirculation system, bypassing the vaporizer 20, by activating flush valve 38.

The recirculation system 200 communicates with a patient via inhalation line 40 and exhalation line 42, which are connected to a breathing mask or other patient interface. When the patient inhales, the inhalation valve 24 opens to permit inhalation of the oxygen/anesthesia gas mixture. At this time, the exhalation valve 28 closes the exhalation line 42. As the patient exhales, the inhalation valve closes the inhalation line and the exhalation valve opens the exhalation line to direct the exhaled gas through the carbon dioxide absorber 30. The processed exhaled gas (which will contain oxygen and anesthesia gas) that exits the outlet of the carbon dioxide absorber 30 is merged with the fresh oxygen/ anesthesia gas mixture and circulated to the patient via the inhalation line 40.

The pressure relief valve 26 vents gas from the breathing system when the pressure exceeds the threshold level set by the user. The manometer 22 provides a visual reading of the pressure in the breathing system, and the breathing bag 32 provides an expandable volume for accommodating the exhaled and fresh gas entering the system.

The interconnections of the various components illustrated in FIG. 2 are shown in FIGS. 3 and 4A–4C. As shown in FIGS. 4A and 4B, the manifold 12 has an internal oxygen channel 43 formed therein. Outlet ports of the flowmeters 16 and 18 are threadably secured to the manifold 12 and communicate with the oxygen channel 43 via ports 44 and 46. Inlet ports (not shown) of the flowmeters 16 and 18 are connected to the oxygen source 36 (FIG. 2) with tubing.

In an exemplary embodiment, flowmeter 16 provides a variable flow rate of up to one liter per minute (l/min.), while flowmeter 18 provides a variable flow rate of up to five l/min. As a result, the combination of flowmeters 16 and 18 can provide a precise oxygen flow rate of between zero to six l/min. Various combinations of flowmeters may be used, however, and only one flowmeter may be used if desired.

Figure 3:
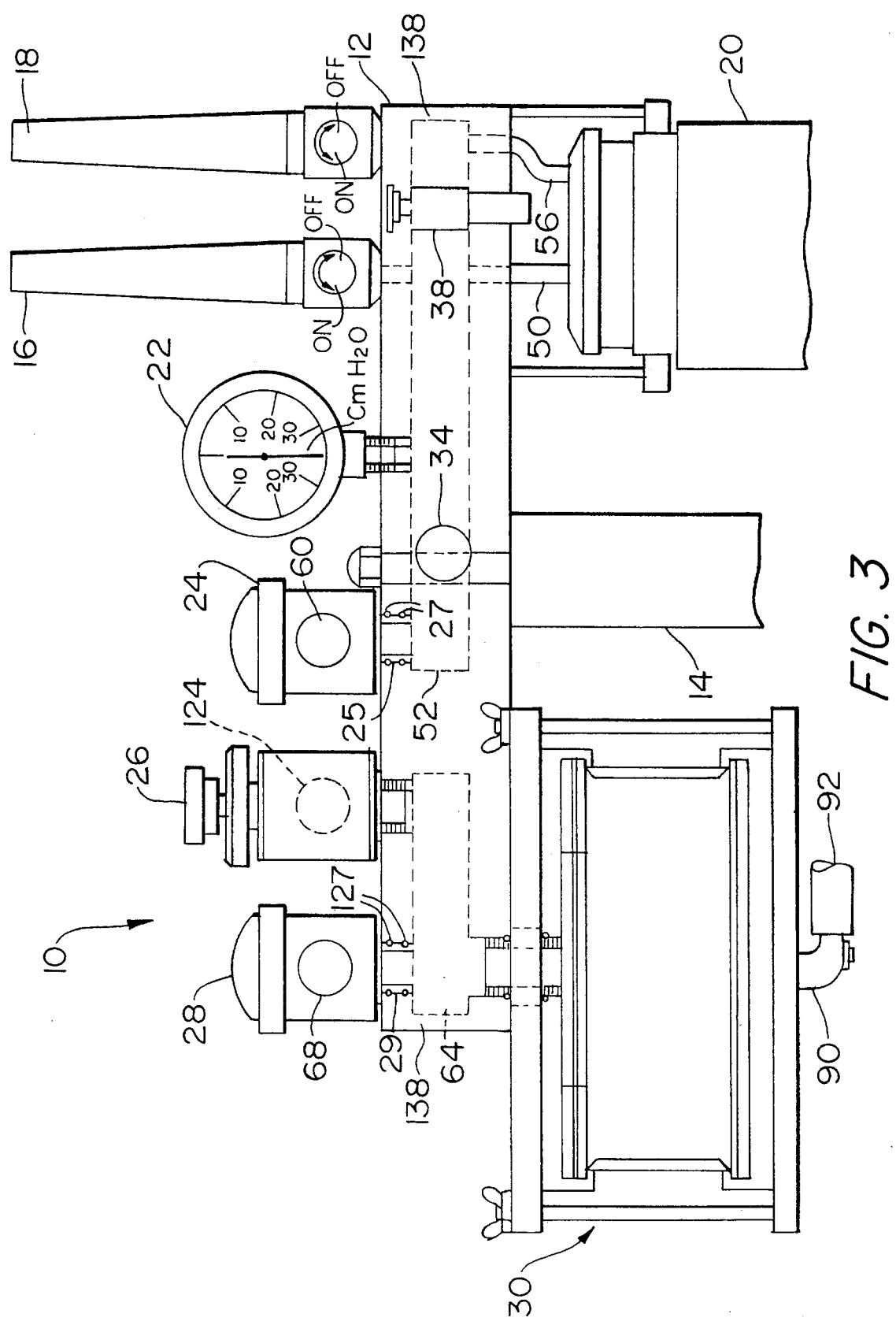
FIG. 3 is a front view of the anesthesia machine of FIG. 1 showing the internal channels of a manifold.

Oxygen flows out of the oxygen channel 43 through outlet port 48, which is flow connected to an inlet of the vaporizer 20 with tubing 50, as shown in FIG. 3. The vaporizer 20 mixes the oxygen with isoflourine (or some other known anesthestic) and the mixture passes through tubing 56 (FIG. 3) and enters an internal inlet channel 52 formed in the manifold through port 54. Pure oxygen may also enter the inlet channel 52 via port 55 when the flush valve 38 is activated.

The inhalation valve 24 flow communicates with the inlet channel via port 58. An outlet port 60 of the inhalation valve 24 is coupled to the inhalation line 40, which carries the gas mixture to the patient.

The breathing bag 32 is flow connected to the inlet channel 52 via port 34. The breathing bag 32 inflates as the patient exhales and deflates as the patient inhales, and allows for "bagging" of the patient if necessary.

The manometer 22 is also flow connected to the inlet channel 52 via port 62. The manometer 22 provides a visual reading of the pressure in the breathing system and assists in setting the desired pressure threshold setting of the pressure relief valve 26. The manometer allows for pressure readings between 0 and 30 centimeters of water with an expanded scale from 0 to 10. Conventional manometers for anesthesia machines typically have a range from 0 to 60 centimeters of water. However, pressure readings of up to 30 centimeters of water are more than adequate, particularly since pressures above 20 centimeters of water may detrimentally affect the patient's lungs. Furthermore, since the normal breathing pressure in the breathing system is approximately 1.5 centimeters of water, the finely-calibrated manometer of the present invention provides a much more precise pressure reading than conventional manometers.

An internal outlet channel 64 is also formed within the manifold and receives exhaled gas from the patient. As shown, in FIGS. 3, 4B, and 4C, the exhalation valve 28 flow communicates with the outlet channel 64 via port 66 and has an inlet port 68 coupled to the exhalation line 42.

The outlet channel 64 directs exhaled gas into the carbon dioxide absorber 30 through inlet port 70. As embodied herein and shown in FIG. 5, the carbon dioxide absorber 30 includes a cylindrical casing 72, composed of clear plastic or glass, sandwiched between upper and lower mounting plates 74 and 76. The casing 72 is open at its upper and lower ends, and the upper and lower edges may be chamfered.

End caps 78 are attached to the lower surface of the upper mounting plate 74 and the upper surface of the lower mounting plate 76. Each end cap includes an interior groove for supporting two seals 80, such as neoprene gaskets, with a sieve or filter 82 sandwiched therebetween. The casing 72, end caps 78, and seals 80 form an airtight cannister for containing a material, such as calcium hydroxide, that readily absorbs carbon dioxide from the exhaled gas flowing through the cannister, as indicated by the arrows. The calcium hydroxide converts to calcium carbonate as it absorbs carbon dioxide and is discarded periodically when saturated.

Rods 84, with permanently attached wing nuts 86, extend from the upper mounting plate 74 and are received in and secured to threaded openings in the lower mounting plate 76. During assembly, the casing 72 is placed on the seal 80 supported by the lower mounting plate 76 and end cap 78, and the rods 84 are inserted into openings in the upper mounting plate 74 and are threaded into the threaded openings in the lower mounting plate by turning the wing nuts 86. The rods and openings and the upper and lower mounting plates cooperate to precisely and easily align the top and bottom mounting plates and casing to ensure an airtight cannister. The openings in the lower mounting plate may also be chamfered to further facilitate insertion of the rods.

An inlet port 88 is formed in the upper mounting plate 74 and includes a threaded shank for flow connecting the cannister to the outlet channel 64 via port 70, as shown in FIGS. 3 and 4C. An outlet port 90 is formed in the lower mounting plate 76 and flow connects the cannister to the inlet channel 52 via tubing segment 92 and port 94 (FIGS. 4B and 4C) to merge the flow of processed exhaled gas with the fresh oxygen/anesthesia gas mixture. A bleed valve 93 may be connected to port 90 to drain moisture from within the cannister.

The pressure relief valve 26 flow communicates with the outlet channel 64 via port 96. As embodied herein and shown in FIG. 6, the pressure relief valve 26 includes a threaded shank 98 that engages threaded port 96 to secure the pressure relief valve 26 to the manifold 12. The pressure relief valve 26 also includes a housing having an outer wall 102 and an inner wall 104 that defines a chamber 106 in flow communication with the outlet channel 64 via an opening in a valve seat 108.

A plastic poppet 110 is normally biased against the valve seat 108 by a coil spring 112. A pressure adjustment knob 114 includes a shaft 116 that threadedly engages to an upper portion of the inner wall 104. The shaft is hollow and includes an inner lip 118 for engaging one end of the coil spring 112. A piston 117, with an O-ring 119 lodged in an annular groove, surrounds and guides the lower portion of the shaft 116 relative to inner wall 104.

A user sets the predetermined pressure level by rotating the knob 114 to compress spring 112, whose lower end is seated against poppet 110. Rotation of the knob 114 varies the compression of the spring 112 and thus the biasing force adjustably acting to hold the poppet 110 in a valve closure position against valve seat 108. The shaft 116 is preferably finely threaded to precisely adjust the pressure level.

Figure 6:
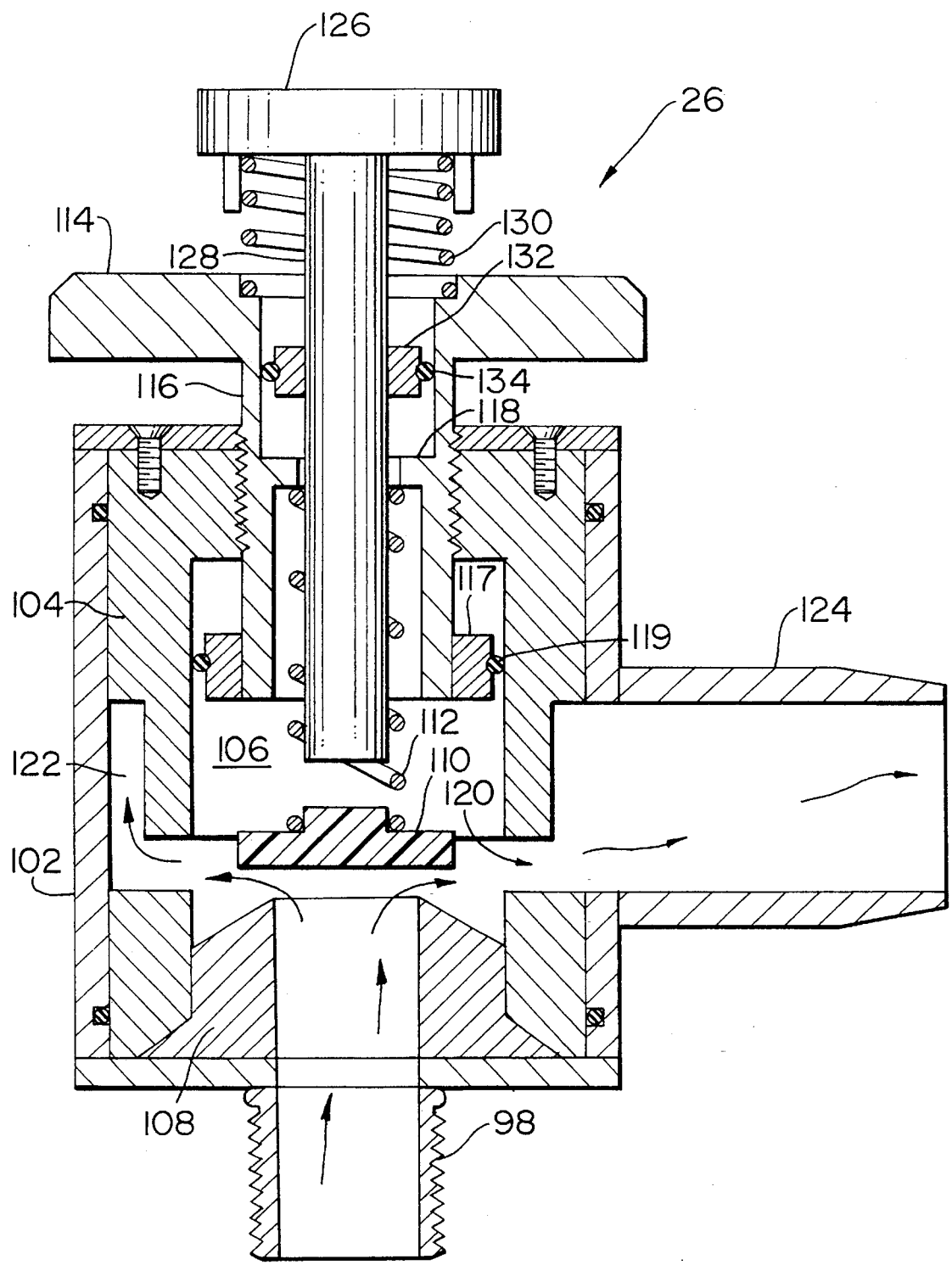
FIG. 6 is a sectional view of a pressure relief valve for the anesthesia machine of FIG. 1.

When the pressure in the breathing system exceeds the desired threshold set by the pressure adjustment knob 114, the poppet 110 is lifted from the valve seat 108, as shown in FIG. 6, thus allowing gas to enter the chamber 106. The inner wall 104 includes circumferentially elongated ports 120, as shown in FIG. 7, which communicate with a channel formed between the inner and outer walls to define an annular flow path 122. The flow path 122 communicates with a vent 124 through which pressure-relieving gas is vented to a vacuum line (not shown) or other location preferably leading away from operating room personnel.

The pressure relief valve also includes vent override means for preventing the flow of gas into the chamber independent of the pressure in the breathing system without changing the pressure threshold setting. As embodied herein and shown in FIG. 6, the vent override means includes a plunger 126 having a shaft 128 positioned within the hollow shaft 116 and coil spring 112. A spring 130, disposed between the adjustment knob 114 and the top of the plunger 126, biases the plunger 126 in a direction away from the pressure adjustment knob 114 and out of contact with the poppet 110. A plunger piston 132, with an O-ring 134 lodged in an annular groove, stabilizes plunger reciprocating motion within the shaft 116.

When "bagging" is necessary, the user depresses the plunger 126 into contact with the poppet 110 to maintain the poppet 110 against the valve seat 108, thus preventing the flow of gas into the chamber 106 even if the pressure in the breathing system exceeds the threshold setting set by the pressure adjustment knob. When "bagging" is completed, the user releases the plunger 126 and the pressure relief valve is returned to the established pressure threshold setting. As a result, there is no need to manipulate the pressure adjustment knob to reset the pressure threshold.

Various alternatives of the vent override means are possible. For example, the valve seat may include a slot below the poppet for receiving a slidable member that is movable by the user. To override the pressure relief valve, the user slides the member into position blocking the opening of the valve seat communicating with the breathing system. Other embodiments will be readily apparent to those skilled in the art.

The various components of the anesthesia machine 10 must be cleaned periodically to remove residue and other potential contaminants. To facilitate cleaning, each of the internal channels in the manifold includes, as shown in FIGS. 3 and 4A–4C, a cleaning port 136 that is closed with a cap 138 during use. When cleaning is desired, the caps 138 are removed, allowing access to the cleaning ports. Since the internal channels preferably consist of straight, cylindrical sections formed by boring or molding, they can be easily cleaned with a brush or other cleaning means.

To further facilitate cleaning, the components of the anesthesia machine, including the inhalation and exhalation valves 24 and 28, the pressure relief valve 26, the manometer 22, and the flowmeters 16 and 18 may be removed from the manifold for cleaning of their respective ports. Furthermore, as shown in FIG. 3, the inhalation and exhalation valves include stems 25 and 29, and O-rings 27, that are friction fitted within the ports 58 and 66 (FIG. 4C). As a result, these valves can be rotated relative to the manifold during use with the O-rings 27 providing an effective seal. Although the pressure relief valve, flowmeters, and manometer are shown as threadably secured to the manifold, these components may also be attached to the manifold in a manner similar to the inhalation and exhalation valves.

Rotation of the exhalation and inhalation valves relative to the manifold also assists in preventing kinking of the inhalation and exhalation lines leading to the patient. The outlet ports of the inhalation and exhalation valves may also be angled downward (e.g., 45° downward) to further prevent kinking of the lines since the manifold is typically higher than the patient during surgery.

It will be apparent to those skilled in the art that various modifications and variations can be made in the apparatus of the present invention without departing from the scope or spirit of the invention. Thus, it is intended that the present invention cover the modifications and variations of this invention provided they come within the scope of the claims and their equivalents.

What is claimed is:

1. An anesthesia machine, comprising:

a breathing system for channeling inhalation and exhalation gases; and a pressure relief valve having a housing that defines a chamber in flow communication with the breathing system, a valve member for regulating a flow of gas from the breathing system into the chamber and venting gas into the chamber when pressure in the breathing system exceeds an adjustable predetermined pressure threshold setting, and a plunger normally biased by a biasing means to a first position out of contact with the valve member and depressible to a second position in contact with the valve member to close the valve member when a force is applied to the plunger to override the predetermined pressure threshold setting and prevent the flow of gas into the chamber, the plunger being returned to the first position by the biasing means when the force is removed therefrom to reestablish the same predetermined pressure threshold setting in the breathing system and allow venting of gas into the chamber when the pressure in the breathing system exceeds the predetermined pressure threshold setting.

2. The machine of claim 1, wherein the breathing system includes a manifold having a first internal channel for receiving the inhalation gas and a second internal channel for receiving the exhalation gas.

3. The machine of claim 2, wherein the pressure relief valve is removably secured to the manifold in flow communication with the second internal channel.

4. The machine of claim 2, wherein the manifold further includes a port for flow connecting the pressure relief valve to the second internal channel and securing the pressure relief valve to the manifold.

5. The machine of claim 2, wherein the manifold further includes a third internal channel for receiving oxygen and a vaporizer connecting the third internal channel and the first internal channel in flow communication, the vaporizer mixing the oxygen with an anesthetic gas.

6. The machine of claim 1, further including a carbon dioxide absorber in flow communication with the breathing system, the carbon dioxide absorber including a cannister comprising a casing open at its top and bottom ends, first and second mounting plates for covering the top and bottom ends of the casing, a first seal supported by the first mounting plate and a second seal supported by the second mounting plate, and a plurality of rods secured to and extending from one of the first and second mounting plates and receivable in openings in the other of the first and second mounting plates for joining the mounting plates with the casing therebetween, the first and second seals engaging top and bottom edges of the casing to effectively seal the cannister.

7. The machine of claim 6, wherein the cannister has an inlet port flow connected to the second internal channel and an outlet port flow connected to the first internal channel.

8. The machine of claim 6, wherein the top and bottom edges of the casing are chamfered.

9. The machine of claim 6, wherein the first and second mounting plates each include a groove for supporting the first and second seals.

10. The machine of claim 6, wherein the first and second mounting plates each include ports for flow connecting the cannister to the breathing system.

11. The machine of claim 2, wherein each of the first and second internal channels includes a port formed in the manifold and having an opening flush with an outer surface of the manifold.

12. The machine of claim 11, wherein at least one of a pressure relief valve, an inhalation valve, an exhalation valve, and a manometer includes a stem receivable in the port, the stem including at least one O-ring for providing sealing engagement with the manifold when the stem is received in the port.

13. The machine of claim 2, wherein each of the first and second channels includes at least one cleaning port closed by a removable cap.

14. The machine of claim 13, wherein the first and second channels are cylindrical.

15. A pressure relief valve for a breathing system of an anesthesia machine, comprising:

a housing that defines a chamber in flow communication with the breathing system;

a valve member for regulating a flow of gas from the breathing system rate the chamber and venting gas into the chamber when pressure in the breathing system exceeds an adjustable predetermined pressure threshold setting; and a plunger normally biased by a biasing means to a first position out of contact with the valve member and depressible to a second position in contact with the valve member to close the valve member when a force is applied to the plunger to override the predetermined pressure threshold setting and prevent the flow of gas into the chamber, the plunger being returned to the first position by the biasing means when the force is removed therefrom to reestablish the same predetermined pressure threshold setting in the breathing system and allow venting of gas into the chamber when the pressure in the breathing system exceeds the predetermined pressure threshold setting.

16. The valve of claim 15, wherein the pressure relief valve further comprises a valve seat through which gas flows from the breathing system into the chamber and the valve member comprises a poppet biased against the valve seat by an adjustable biasing force that establishes the pressure threshold setting.

17. The valve of claim 11, wherein the pressure relief valve further comprises a coil spring for biasing the poppet against the valve seat and an adjustment knob for varying the biasing force by changing the compression of the spring.

18. The valve of claim 17, wherein the plunger is movably attached to the adjustment knob and biased in a direction away from the poppet.

19. The valve of claim 17, wherein the plunger is supported within an opening extending through the adjustment knob and is coaxial with the coil spring.

20. The valve of claim 15, further comprising a vent in flow communication with the chamber for directing gas out of the chamber.

21. The valve of claim 15, wherein the housing includes an inner wall defining the chamber and an outer wall surrounding the inner wall with a gas flow path therebetween, the inner wall including at least one port for flow connecting the chamber with the gas flow path.

22. The valve of claim 21, further comprising a vent in flow communication with the gas flow path for directing gas out of the chamber.

23. A pressure relief valve for controlling pressure in a system, comprising:

a housing that defines a chamber in flow communication with the system;

a valve sent in the chamber;

a valve member biased against the valve seat by an adjustable biasing force to establish a predetermined pressure threshold setting in the system, the valve member being unseated from the valve seat when pressure in the system exceeds the predetermined pressure threshold setting to reduce pressure in the system; and a plunger normally biased by a biasing device to a first position out of contact with the valve member, to allow the valve member to regulate pressure in the system in accordance with the predetermined pressure threshold setting and movable to a second position when a force is applied to the plunger for engaging and maintaining the valve member seated against the valve seat to override the predetermined pressure threshold setting, the plunger being returned to the first position by the biasing device when the force is removed therefrom to reestablish the same predetermined pressure threshold setting in the system and allow regulation of the pressure in the system in accordance with the predetermined pressure threshold setting.

24. The valve of claim 23, further comprising a pressure adjustment member threadably secured to the housing, the pressure adjustment member capable of adjusting the biasing force on the valve member when rotated relative to the housing.

25. The valve of claim 24, wherein the pressure adjustment member includes an inner surface defining a central bore, the plunger slidably disposed within the central bore.

26. The valve of claim 25, further comprising a seal surrounding a portion of the plunger and contacting the inner surface of the pressure adjustment member to prevent gas in the chamber from escaping through the central bore.

27. The valve of claim 24, wherein the biasing device comprises a spring having one end supported by the pressure adjustment member and an opposite end engaging the plunger to bias the plunger to the first position.

28. The valve of claim 23, wherein a portion of the plunger is slidably disposed in the housing.

* * * * *

UNITED STATES PATENT AND TRADEMARK OFFICE
CERTIFICATE OF CORRECTION

PATENT NO.  : 5,568,910
DATED       : October 29, 1996
INVENTOR(S) : Raymond KOEHLER and James E. DONALDSON It is certified that error appears in the above-indentified patent and that said Letters Patent is hereby corrected as shown below:

Claim 15, line 6 (col. 9, ln. 2), change "rate" to --into--.

Col. 10, Claim 23, line 5, change "sent" to --seat--.

Signed and Sealed this

Fourteenth Day of January, 1997

Attest:

BRUCE LEHMAN

*Attesting Officer*  *Commissioner of Patents and Trademarks*